United States Patent [19]

Gomez et al.

[11] 4,104,367

[45] Aug. 1, 1978

[54] RADIOIMMUNOASSAY FOR METHADONE

[75] Inventors: Magdalena Usategui Gomez, Wayne; Harvey Gurien, Irvington; John Edward Heveran, Fairfield; Manfred Weigele, North Caldwell, all of N.J.

[73] Assignee: Hoffmann-La Roche Inc., Nutley, N.J.

[21] Appl. No.: 731,620

[22] Filed: Oct. 13, 1976

[51] Int. Cl.$^2$ .................. G01N 33/16; A61K 43/00
[52] U.S. Cl. .................. 424/1; 23/230 B; 260/112 R; 424/12; 560/180
[58] Field of Search ............ 260/112 R, 485 R, 485 J; 23/230 B; 424/1, 1.5, 12

[56] References Cited

PUBLICATIONS

Landon et al., The Analyst, vol. 101, No. 1201, Apr. 1976, pp. 225–243.

*Primary Examiner*—Richard E. Schafer
*Assistant Examiner*—Christine M. Nucker
*Attorney, Agent, or Firm*—Samuel L. Welt; George M. Gould

[57] ABSTRACT

An improved immunoassay for methadone is disclosed. The subject radioimmunoassay utilizes a novel antigen, antibody and novel labelled methadone derivatives.

15 Claims, No Drawings

RADIOIMMUNOASSAY FOR METHADONE

BACKGROUND OF THE INVENTION

Immunoassays for methadone have been known in the art. Thus, for example in U.S. Pat. No. 3,843,696 an immunoassay for methadone based on enzyme multiplication is described (EMIT). This immunoassay employs an antibody derived from an antigen having the following hapten radical:

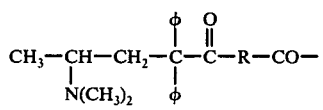

Thus the linkage of the hapten to the immunogenic carrier is seen to occur at the ketone end of the molecule. The resulting antibody cross-reacts slightly with the methadone metabolite 2-ethylidene-1,5-dimethyl-3,3-diphenylpyrrolidine.

General reference to the present immunoassay has been made in two publications. These are Cleeland et al., *Clinical Chemistry,* 22, 712(1976) and Manning et al., *Journal of Forensic Sciences,* 21, 112 (1976). The aforesaid papers deal mainly with the results of clinical testing of the present assay.

DESCRIPTION OF THE INVENTION

The present invention relates to an improved immunoassay for methadone. In particular the present invention relates to a radioimmunoassay for methadone employing a novel antigen, antibody and radiolabelled methadone derivative.

In one aspect of the present invention a methadone derivative of the formula

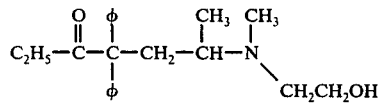

wherein $\phi$ is phenyl
is utilized to prepare novel haptens of the formula

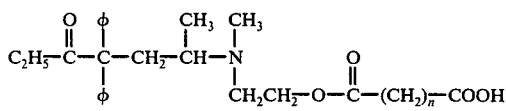

wherein $\phi$ is as above and $n$ is an integer selected from 2 or 3.

The conversion of compounds of formula I to form the haptens of formula II is carried out in a manner known per se for forming hemi-esters by the reaction of a lower alkanoic dicarboxylic acid anhydride with the compound of the formula I. Suitable lower alkanoic dicarboxylic acid anhydrides are succinic anhydride (forming a compound of formula II where $n$ is 2) and glutaric anhydride (forming a compound of formula II where $n$ is 3). The reaction is carried out in a polar organic solvent such as dimethylformamide, dimethylsulphoxide or pyridine. A reaction temperature of from 50° to 120° C., preferably in the range of 100°–110° C. is employed. Usually a base is present in the reaction mixture. Suitable bases include triloweralkylamines such as triethylamine or an alkoxide salt with an alkali metal such as potassium t-butoxide.

In order to prepare the antigen of the present invention, it is necessary that the hapten of formula II be covalently bonded through the carboxylic group to a conventional immunogenic carrier material.

As used herein, the term "immunogenic carrier material" is meant to include those materials which have the property of independently eliciting an immunogenic response in a host animal and which can be covalently coupled to the above described hapten. Suitable carrier materials include, for example, proteins; natural or synthetic polymeric compounds such as polypeptides, e.g., polylysine or copolymers of amino acids; polysaccharides; and the like. Particularly preferred carrier materials are proteins and polypeptides; especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin, and bovine gamma globulin. Other suitable protein products will be suggested to one skilled in the art. It is generally preferred but not necessary that proteins be utilized which are foreign to the animal hosts in which the resulting antigens will be employed.

The covalent coupling of the hapten to the immunogenic carrier material can be carried out in a manner well known in the art. For example, the hapten can be converted to an isolatable activative form prior to coupling. Suitable activated forms include the N-hydroxysuccinimide ester, p-nitrophenyl ester; acylimidazoles; and so forth. Other methods for coupling may be employed wherein the activated intermediates need not be isolated. Such methods include the mixed anhydride method, use of EEDQ (N-ethoxycarbonyl-2-ethoxy-1,2-dihydroquinoline) as coupling agent and the like.

The coupling of the hapten either as the free acid or as an activated derivative to the immunogenic carrier material can be readily accomplished utilizing techniques well known in the art for establishing amide bonds. Thus, for example, one such technique would involve dissolving the carrier material and a coupling agent in a suitable inert solvent followed by adding the hapten. The reaction may be conducted in a temperature in the range of from about 0° C. to about 50° C. although higher or lower temperatures might be employed depending on the nature of the reactants. A most preferable temperature is about room temperature.

The coupling agent which may be used in the aforesaid reaction will be selected from those commonly employed in organic chemistry for initiating amide bond formation. A particularly suitable group of coupling agents comprise the carbodiimides, most preferably dicyclohexylcarbodiimide or 1-ethyl-3-(3-dimethylaminopropyl) carbodiimide either as the free base or as the mineral acid addition salt, such as the hydrochloride. The molar ratio of the hapten to the carrier material will, of course, depend on the identity of the hapten utilized and the protein selected for the reaction.

Conventional conditions for the coupling reaction can be employed. Thus when utilizing carbodiimides as coupling agents, it is desirable to utilize a slightly acidic reaction medium for this step, e.g., a medium having a pH in the range of from about 3 to 6.5, most preferably in the range of from about 4 to 6.5. Upon completion of the reaction, the excess hapten molecules may be removed by dialysis.

As indicated previously, one technique for preparing the antigens of the present invention is to first prepare and isolate an activated derivative and then to react this compound with the carrier material to form the antigen. Such activated derivatives are conveniently prepared by reacting the hapten with a desired activating compound, such as N-hydroxysuccinimide, and a coupling agent, such as dicyclohexylcarbodiimide, in an inert solvent. The reaction is usually allowed to proceed for 16–60 hours at reduced temperatures (0°–5° C.). The activated derivative may then be isolated by filtering off the by-product, dicyclohexylurea, and distilling off the solvent.

The hapten may then be coupled to the carrier material by contacting the activated derivative with the chosen carrier material. When the activated derivative is the N-hydroxysuccinimide ester and the carrier material is bovine serum albumin, this may be accomplished by adding the activated derivative in a water-miscible solvent to an aqueous solution of the carrier material containing a base, such as sodium bicarbonate.

Another method of coupling carrier protein to hapten is by activating the carboxyl group of the hapten without isolation of an intermediate and adding the activated hapten to the carrier protein. An example of such a reaction is the mixed anhydride obtained by reaction with isobutylchloroformate. The hapten is dissolved in an anhydrous, water-miscible organic solvent, such as dioxane or 1-methyl-2-pyrrolidinone, and the solution is neutralized with an equimolar quantity of triethylamine. After stirring at room temperature, the temperature of the mixture is reduced to between 0° and 8° C. An equimolar quantity plus 10% excess of isobutylchloroformate is then added and stirring is continued. Meanwhile, the carrier protein, e.g., bovine serum albumin, is dissolved in water and the pH is adjusted to 9.0 with NaOH. The quantity of carrier used is approximately equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight.

The mixture is then dialyzed and the antigen recovered from the dialysis bag.

The antigens of the present invention may be utilized to induce formation of antibodies specific to methadone and related compounds in host animals by injecting the antigen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with methadone or an antigen prepared from a derivative thereof, as described above.

The specific antibodies of the present invention are useful as reagents for the determination of methadone. In such an assay, a known amount of a radiolabeled methadone derivative such as $^{125}$I-N-2-(4-hydroxyphenyl)-ethyl succinamic acid, N-methyl-N-[1-methyl-3,3-diphenyl)-4-oxohexyl]aminoethanol ester or $^{125}$I-6-dimethylamino-4-phenyl-4-(4-hydroxyphenyl)heptan-3-one is mixed with the above antibody and a sample containing some methadone is added. The amount of methadone in the sample can be determined by measuring the inhibition of the binding to the specific antibody of the labeled methadone derivative by the unknown sample and comparing such value to a standard curve obtained by utilizing known amounts of methadone with the antibody-labeled antigen mixture and determining the inhibition of binding for each such amount. The reagents may be added in any order. A suitable assay procedure for this purpose is described in greater detail in U.S. Pat. No. 3,709,868. A particularly preferred labeled methadone derivative is $^{125}$I-6-dimethylamino-4-phenyl-4-(4-hydroxyphenyl)heptan-3-one due to its stablity even on storage at room temperature for extended periods.

The novel antigens and antibodies of the present invention may be utilized in conjunction with conventional additives, buffers, stabilizers, diluents, or in combination with other physiologically active substances. The preparation and use of compositions containing antigens or antibodies in conjunction with physiologically acceptable adjuvants is now well known in the art.

The compounds and intermediates of the present invention may be utilized as free bases or acid addition salts. Suitable addition salts include the hydrochloride, hydrobromide, sulfate, nitrate, phosphate, trifluoroacetate, oxalate and the like.

EXAMPLE 1

Preparation of
6-dimethylamino-4-(4-hydroxyphenyl)-4-phenyl heptan-3-one hydrobromide Into a 100 ml flask equipped for stirring, under a nitrogen atmosphere are placed 0.55g of 6-dimethylamino-4-(4-methoxyphenyl)-4-phenyl-heptane-3-one, 40 ml of methylene chloride and 12.1 ml of a solution of boron tribromide/methylene chloride (10% solution obtained commercially). The mixture was allowed to stir at room temperature overnight. Thereafter, 30 ml. of methanol was added with cooling. The residual oil, obtained upon removing the solvent at reduced pressure, was treated with 7 ml of water, whereupon the crude product crystallized. After filtration and washing with water, the solid was recrystallized from water to give 0.137 g of the above captioned product m.p. 246°–247.5° C. Concentration of the aqueous filtrate yielded a small second crop of 20 mg.

Analysis: Calculated: C, 62.07; H, 6.95; N, 3.45. Found: C, 62.33; H, 6.87; N, 3.21.

EXAMPLE 2

Preparation of
N-methyl-N-(1-methyl-3,3-diphenyl-4-oxohexy) aminoethanol hydrobromide Into a 500 ml three necked flask equipped with a stirrer, nitrogen gas inlet, thermometer, dropping funnel and takeoff were added 45.5 ml of 3N ethyl magnesium chloride (0.136 mol) and 54 ml of anhydrous ether. There was alowly added a solution of 10.1 g. of 4-(N-methyl,N-[2-hydroxyethyl])amino-2,2-diphenylpentan nitrile (0.0328 mol) in 81 ml of dry toluene. The reaction was mildly exothermic. The reaction mixture was then heated and the ether distilled off. When the reaction temperature reached 100° C., the takeoff was removed and the reaction mixture was refluxed with stirring for 8 hours.

There was then added dropwise a total of 95.5 ml of 2N of HCl with a very exothermic reaction. Ther reation mixture was then refluxed and stirred for 4 hours.

After cooling, the solution was transferred to a separatory funnel and the aqueous layers removed. The organic layer was washed with 70 ml. of 2N HCl. The combined aqueous layers were backwashed with 70 ml of toluene. The aqueous layer was then adjusted to pH 8 with concentrated NH₄OH and extracted with 2 × 100 ml of chloroform. The organic extract was dried over CaSO₄, filtered and concentrated. After further concentration at high vacuum, the residue was taken up in absolute ethanol and treated with dilute aqueous HBr. The solution was concentrated to a tan oil which was taken up in absolute ethanol, concentrated to one-half volume and the solution treated with anhydrous ether until turbid. The mixture was stored in a freezer, then filtered and the solid washed with a mixture of absolute ethanol/anhydrous ether. The above-captioned product obtained after drying at high vacuum over $P_2O_5$ had a melting point of 148° C. I.R. and NMR spectra were compatible for a keto alcohol structure.

Elemental Analysis: Calc. C, 62.86; H, 7.19; N, 3.33; Br, 19.00. Found C, 62.56; H, 7.21; N, 3.29; Br, 19.12.

Additional crops of product can be obtained from the ethanol/ether mother liquors by adding additional anhydrous ether.

EXAMPLE 3

Preparation of Succinic Acid, N-methyl-N(1-methyl-3,3-diphenyl-4-oxohexyl) aminoethanol monoester To a solution of 210 mg. of N-methyl-N-(1-methyl-3,3-diphenyl-4-oxohexyl) aminoethanol hydrobromide in 5 ml of dry pyridine was added 56 mg. of potassium t-butoxide. After stirring at room temperature for 15 min., 200 mg. of succinic anhydride was added. The mixture was heated to 100° and stirred at this temperature for 1 hr. 45 min. It was then evaporated under reduced pressure and the residue was chromatographed on silica gel. After developing the column with ether, ethyl acetate and acetone, fractions containing the desired product were eluted with acetone/methanol (4:1). Upon evaporation, there were obtained 207 mg. of the hemisuccinate as a colorless hygroscopic solid.

EXAMPLE 4

Preparation of N-2-(4-hydroxyphenyl)ethylsuccinamic acid, N-methyl-N-(1-methyl-3,3-diphenyl-4-oxohexyl)aminoethanol ester To a solution of 440 mg. of succinic acid, N-methyl-N-(1-methyl-3,3-diphenyl-4-oxohexyl)aminoethanol monoester in 5 ml of dry tetrahydrofuran was added 162 mg. of carbonyldiimidazole. The reaction mixture was stirred at room temperature for 1 hr. Then 137 mg. of tyramine was added. After stirring for another 16 hr. at room temperature, the mixture was evaporated under reduced pressure and the residue was subjected to chromatography on silica gel. The column was developed with ether and ether/ethyl acetate (1:1). Fractions containing the desired product were evaporated in vacuo. There were obtained, 379 mg. of the desired amide as a colorless amorphous solid.

EXAMPLE 5

Preparation of $I^{125}$-N-2-(4-hydroxyphenyl)-ethyl succinamic acid, N-methyl-N [1-methyl-3,3-diphenyl-4-oxophenyl] aminoethanol ester A total of 50µl of a solution of 1 mg of N-2-(4-hydroxyphenyl)-ethyl succinamic acid, N-methyl-N-[1-methyl-3,3-diphenyl-4-oxohexyl] aminoethanol ester in 1 ml of dimethylsulfoxide was added to a vial containing 5µCi $NaI^{125}$ having a specific activity of 11–17 µCi/mg. To this mixture there was then added a total of 40µl of chloramine T solution (5 mg/ml). The reaction mixture was mixed on a Vortex mixer for 5 minutes. After thorough mixing, a total of 40µl of a 10 mg/ml solution of sodium meta bisulfite was added into the reaction vial and the vial was mixed for 2 minutes on the Vortex mixer to stop the reaction.

The mixture was removed from the vial and placed in a small bottle containing 2 ml of Tris buffer pH 6.5 with 1% human albumin. The mixture is then placed on the surface of a 100–200 mesh Bio Gel P-Z column (2.6 × 24 cm) until completely absorbed on the column material. A total of 2 ml of Tris buffer with 1% human albumin was added to the column and the column was then eluted with Tris buffer with 1% human albumin and 60 × 5 ml fractions were collected at a flow rate of 25 ml/hr. Fractions #12–18 were pooled and the resulting combined elute contained the above captioned labeled antigen having a radioactive concentration of 6.7µCi/ml.

EXAMPLE 6

Preparation of $I^{125}$-6-dimethylamino-4-phenyl-4-(4-hydroxyphenyl)-heptan-3-one The procedure of Example 5 is repeated using the methadone derivative 6-methylamino-4-phenyl-4-(4-hydroxyphenyl)heptan-3-one except for the following modifications. Instead of mixing the $NaI^{125}$ reaction mixture on a Vortex mixer the mixture is shaken gently for 90 seconds and after addition of the bisulfite the mixture is shaken gently for 30 seconds. Finally 2.0 ml of 0.1 M Tris buffer pH 7.0 is used prior to the column chromatography step. The resulting above-captioned labeled antigen is obtained in Fractions #22–27 at a radioactive concentration of 10.5µCi/ml.

EXAMPLE 7

Preparation of Immunogen

To 40 ml of acetate buffer (0.05M, pH 5.5) containing 200 mg. of bovine serum albumin (crystalline) was added 150 mg. of the hemisuccinate hapten prepared in Example 3. A total of 150 mg. of the water soluble carbodiimide 1-ethyl-3-(3-dimethylaminorpropyl) carbodiimide. HCl was then added to the solution and stirred continuously for 24 hours at room temperature. The pH was periodically monitored and maintained at 5.5. The final solution was dialyzed in the cold against distilled water for 3 days. The desired antigen was isolated from the dialysis bag.

EXAMPLE 8

Test Procedure for the $^{125}I$ radioimmunoassay for Methadone

Urine specimens require no special handling. Pipetted samples should be free of gross debris.

All reagents should be brought to ambient temperature before use.

All pipetting must be done precisely.

Qualitative Assay:
1. Set up and label as many tubes (10 × 75 mm glass test tubes recommended) as are required for the Methadone-positive control and for assays of unknown urine specimens. Because of the importance of control values in determination, it is recommended that the positive control be done in triplicate.
2. Add 0.1 ml. of Methadone-positive urine control (100 ng/ml) to each of three tubes.
3. Add 0.1 ml. of each unknown urine specimen to remaining numbered tubes.
4. Add 0.2 ml of antigen test reagent, comprising 54,000 DPM in phosphate pH 7.2 buffer, mix well on Vortex mixer.
5. Add 0.2 ml of the antibody test reagent comprising a 1/40 titer in phosphate pH 7.2 buffer containing 50% normal goat serum to each tube; mix well on Vortex mixer.
6. Incubate tubes at ambient temperature for 1 hour.
7. Add 0.5 ml of supernatant fluid from saturated ammonium sulfate solution to each tube to precipitate globulins; mix well on Vortex mixer.
8. Allow tubes to stand at ambient temperature for a minimum of 10 minutes to complete precipitation.
9. Centrifuge for 10 minutes, at approximately 1200 to 2500 × g with a swinging bucket rotor, or at 3500 to 4000 × g with fixed angle head rotor. (Swinging bucket rotor is preferable).
10. Withdraw 0.5 ml of supernatant fluid from each tube without disturbing precipitate along sides or at bottom (supernatant fluid must be clear). Transfer to gamma scintillation vial for counting (alternatively remove fluid and count pellet).
11. Count each tube in gamma scintillation counter for one minute to obtain counts per minute (CPM).

Quantitative Test:

The Radioimmunoassay (RIA) for Methadone protocol presented here describes a qualitative test. If there is need of quantitation, the following modification of the above procedure may be used to establish a standard curve in place of only positive controls.

To establish a standard curve: The normal urine control (O ng/ml) is used as the O point on the standard curve and as the diluent for preparing other standard solutions. The Methadone positive control urine contains 100 ng/ml of Methadone and is to be used as that standard. A 1:2 dilution of the 100 ng/ml standard with the normal urine control will provide a 50 ng/ml standard solution. A 1:4 dilution of the 100 ng/ml standard with the normal urine will provide a 25 ng/ml standard solution.

Set up and label 15 (10 × 75 mm) glass test tubes. To tubes #1, 2 and 3, add 0.1 ml each of normal urine controls; to tubes #4, 5 and 6, add 0.1 ml each of the 25 ng/ml Methadone standard; to tubes #7, 8 and 9, add 0.1 ml each of the 50 ng/ml Methadone standard; and to tubes #10, 11 and 12, add 0.1 ml each of the 100 ng/ml standard.

Proceed with steps 4 to 11 in the above protocol.

Set up standard curve as follows: Let the Y (vertical) axis indicate CPM and X (horizontal) axis indicate nanograms per ml Methadone. Plot points showing the average CPM of the three tubes containing normal human urine, the average of the three containing 25 ng/ml standard, the average of the three containing 50 ng/ml standard and the average of the three containing the 100 ng/ml standards. Fit the best line to establish curve.

To assay Methadone quantity: Determine CPM for each urine specimen tested. Read across from Y axis to determine point where CPM value intersects standard curve, then down to X axis to determine ng/ml of Methdadone present in testing urine.

If tested urine value is higher than 100 ng/ml, dilute test specimen 1:10 and 1:100* in normal saline and repeat test. If value now falls within the standard curve, nultiply the ng/ml by the appropriate dilution factor to establish the Methadone value of the undiluted urine.

* In some cases, urine specimens may have to be diluted 1:1000 before CPM value falls within the range of the standard curve.

Evaluation:

Compare counts per minute obtained from each unknown specimen or standard with average CPM obtained from Methadone-positive controls.

Negative Results: The test is negative for the presence of Methadone when the unknown speciman CPM is lower than that of the average CPM of the Methdadone-positive control.

Positive Results: The test is positive when the unknown specimen CPM is equal to or higher than that of the average CPM of the Methadone-positive control.

EXAMPLE 9

The immunoassay of this invention has been evaluated using urines from a random population of "normal" individuals who have received methadone.

In Table 1 is given a summary of the results of assay for methadone using 100 "normal" urines.

Table 1

| Apparent Methadone Concentration in the Urines 100 "Normal" Individuals | |
|---|---|
| No. of individuals | Methadone equivalents ng/ml |
| 90 | 0–10 |
| 9 | 10–40 |
| 1 | 40–60 |

Based on these results, a level of 100 ng. methadone equivalents per ml was chosen to distinguish between a negative and positive urine.

In table 2 are shown the results of assay for methadone in urines from individuals who have been attending a methadone clinic and who by chemical analysis were found to have methadone in their urines.

Table 2

| Apparent concentration of methadone in urines from 118 individuals attending a methadone clinic | |
|---|---|
| No. of individuals | Methadone equivalents ng/ml |
| 46 | ≧500 |
| 58 | 200–500 |
| 11 | 100–200 |
| 1 | 50–100 |
| 2 | <50 |

Using 100 ng methadone equivalents per ml as the cut-off point, 97% of the urines tested were positive.

The above data strongly suggests that the detection rate of methadone users by RIA is quite high.

We claim:

1. An antigen consisting essentially of a methadone derivative radical derived from a compound of the formula

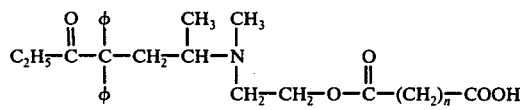

wherein φ is phenyl and n is an integer selected from 2 or 3 covalently bonded through the carboxyl group to an immunogenic carrier material.

2. The antigen of claim 1 wherein said immunogenic carrier material is bovine serum albumin.

3. The angtigen of claim 1 wherein n is 2.

4. A method for the radioimmunoassay of methadone in a sample which method comprises mixing said sample with a known amount of $I^{125}$ radiolabelled methadone derivative selected from the group consisting of $I^{125}$-N-2-(4-hydroxyphenyl)-ethylsuccinamic acid N-methyl-N-[1-methyl-3,3-diphenyl-4-oxohexyl] aminoethanol ester and $I^{125}$-6-dimethylamino-4-phenyl-4-(4-hydroxyphenyl)-hepten-3-one and an antibody which will selectively complex with methadone and said radiolabeled methadone derivative, measuring the degree of binding of the said labeled methadone derivative and determining the amount of methadone present in said sample by comparing said degree of binding to a standard curve obtained by mixing known amounts of methadone with fixed amounts of said labeled methadone derivative and said antibody and determining the degree of binding for each known amount of methadone.

5. The method of claim 4 wherein said radiolabeled derivative is $I^{125}$-N-2-(4-hydroxyphenyl)-ethylsuccinamic acid N-methyl-N-[1-methyl-3,3-diphenyl-4-oxohexyl] aminoethanol ester.

6. The method of claim 4 where said radiolabeled derivative is $I^{125}$- 6-dimethylamino-4-phenyl-4-(4-hydroxyphenyl)heptan-3-one.

7. An antibody specific to methadone elicited by innoculating a host animal with an antigen consisting essentially of a methadone derivative radical derived from a compound of the formula

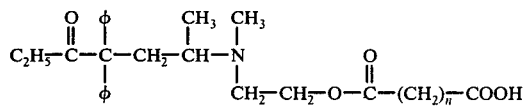

wherein φ is phenyl and n is an integer selected from 2 or 3 covalently bonded through the carboxyl group to an immunogenic carrier material.

8. The antibody of claim 7 wherein the eliciting antigen has n of 2.

9. The antibody of claim 7 wherein the eliciting antigen has bovine serum albumin as the immunogenic carrier material.

10. $I^{125}$-N-2-(4-hydroxyphenyl) ethylsuccinamic acid, N-methyl-N-[1-methyl-3,3-diphenyl-4-oxohexyl] aminoethanol ester.

11. $I^{125}$-6-dimethylamino-4-phenyl-4-(4-hydroxyphenyl)hepten-3-one.

12. A compound of the formula

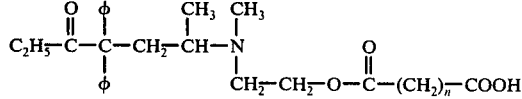

wherein φ is phenyl and n is an integer selected from 2 or 3.

13. The compound of claim 12 wherein n is 2.

14. A compound of the formula

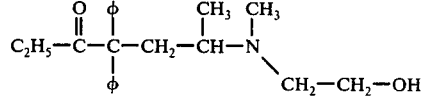

wherein φ is phenyl and acid addition salts thereof.

15. N-2-(4-hydroxyphenyl) ethylsuccinamic acid, N-methyl-N-[1-methyl-3,3-diphenyl-4-oxohexyl] aminoethanol ester and acid addition salts thereof.

* * * * *